United States Patent [19]
Rheinberger et al.

[11] Patent Number: 5,432,130
[45] Date of Patent: Jul. 11, 1995

[54] OPALESCENT GLASS

[75] Inventors: Volker Rheinberger, Vaduz; Wolfram Hoeland; Martin Frank, both of Schaan, all of Liechtenstein

[73] Assignee: Ivoclar AG, Liechtenstein

[21] Appl. No.: 225,719

[22] Filed: Apr. 11, 1994

[30] Foreign Application Priority Data

Apr. 30, 1993 [DE] Germany .................. 43 14 817.4

[51] Int. Cl.6 .............................................. C03C 3/083
[52] U.S. Cl. ...................................... 501/32; 501/63; 501/64; 501/69; 501/70; 106/35
[58] Field of Search ............... 106/35; 501/32, 63, 501/64, 69, 70

[56] References Cited

U.S. PATENT DOCUMENTS

| | | | |
|---|---|---|---|
| 3,709,705 | 1/1973 | Hagedorn | 501/32 |
| 4,298,390 | 11/1981 | Flannery et al. | 501/32 |
| 4,309,219 | 1/1982 | Flannery et al. | 501/32 |
| 4,536,480 | 8/1985 | Flannery et al. | 501/63 X |

FOREIGN PATENT DOCUMENTS 1909187 2/1969 Germany .
632830 1/1988 Japan .
254738 10/1969 U.S.S.R. .

OTHER PUBLICATIONS

Database WPI Section CH, Week 8616 Derwent Class L, AN 86-105800 & SU-A-1 183 471 (Glass Res. Inst.) Oct. 1985.
Chemical Abstracts, vol. 103, No. 2, Jul. 1985 Abstract No. 10377n Seite 261 & SU-A-1 146 288 (State Scientific-Research Institute of Glass) Mar. 1985.
Chemical Abstra ts, vol. 79, No. 14 Oct. 1973 Abstract No. 82824q, Seite 281 & SU-A-379 545 (Lensovet Technological Institute) Apr. 1993.

*Primary Examiner*—Karl Group
*Attorney, Agent, or Firm*—Nixon & Vanderhye

[57] ABSTRACT

An opalescent glass is described which is characterized by a continuous glass phase and a discontinuous glass phase dispersed therein, and which can be used as dental material or as a constituent of dental materials.

10 Claims, No Drawings

OPALESCENT GLASS

The invention relates to opalescent glass and particularly to opalescent glass which, as a result of its chemical resistance and its processing properties, can be used in the dental field.

The property of a material of appearing bluish-white in reflected light and red in transmitted light is called opalescence. A more exact treatment of this effect can be found for example in W. Vogel: Glaschemie, Verlag für Grundstoffindustrie, Leipzig, 1971.

To achieve the opalescence effect with industrial glass, an opacifier is often added to them. Fluorides, phosphates and borates are primarily used as opacifiers.

Opal glasses are for example known from DE-OS 1 496 646. The glasses described there are distinguished through a content of crystallized $TiO_2$ which forms its ownphase and causes a clouding of the glass. The glasses are principally used as pigments in varnishes and paints and as fillers in papers, plastics and chemical fibres.

Known from DE-PS 33 06 648 is a bioactive glass ceramic in whose micro-structure there are apatite and mica crystal phases. The glass ceramic contains no $TiO_2$ or $ZrO_2$. It is intended in particular for prosthetic purposes, namely as bone replacement material.

DE-PS 2 313 074 discloses phosphate-opacified opal glasses based on $SiO_2$-$B_2O_3$-$Al_2O_3$-$K_2O$. It is a disadvantage with these glasses that the opalescence disappears partly or completely when the $Al_2O_3$ content is increased to more than 5 wt. %.

Finally, known from DE-PS 1 909 187 are opal glasses which are likewise free from $TiO_2$ and $ZrO_2$. The opalescence effect of these glasses appears to be attributable to the fact that, after the desired glass objects have been formed, an in-situ phase separation takes place by heat treatment.

The known opal glasses do not however satisfy the requirements which are placed on a dental material. Admittedly, their opalescence effect is sufficient in many cases to imitate the opalescence of natural teeth, but they do not satisfy other requirements for dental materials. For one thing, the conventional glasses frequently contain components which are not completely safe from a physiological point of view. For another, the chemical resistance of the opal glasses is insufficient in many cases for application in the dental field. Finally, the opal glasses known to date have the disadvantage that they do not withstand usual dental processing without losing their original opalescence effect. During the dental processing, the opal glass is comminuted to give a granulate with a particle size of less than 90 μm and the granulate is then sintered at a temperature of up to 1100° C. to give a dense product. Further thermal treatments are optionally carried out at up to 1100° C. After undergoing such processing, conventional opalescent glasses either become completely transparent or they crystallise out very quickly to give a white opaque material. In both cases the desired opalescence effect is completely lost.

It is therefore the object of the invention to provide an opalescent glass, a process for its production and its use, which opalescent glass has a high opalescence and an excellent chemical resistance and, moreover, can withstand the aforementioned dental processing without considerable loss of the original opalescence effect and can therefore be used as dental material.

This object is surprisingly achieved by the opalescent glass according to claims 1 to 3 and the process for its production according to claims 4 to 7 and its use according to claims 8 to 10.

The opalescent glass according to the invention is characterized in that it has a continuous glass phase and a discontinuous glass phase dispersed therein and comprises the following components:

| Component | Wt. % |
| --- | --- |
| $SiO_2$ | 48.0 to 66.0 |
| $B_2O_3$ | 0 to 1.0 |
| $Me(III)_2O_3$ | 5.8 to 20.0 |
| $Me(I)_2O$ | 6.0 to 22.0 |
| $Me(II)O$ | 3.5 to 16.0 |
| $Me(IV)O_2$ | 0.5 to 10.0 |
| $P_2O_5$ | 0.5 to 5.0 |
| $CeO_2$ | 0 to 3.0 | where
a) the quantity of $Me(III)_2O_3$ quoted is formed of 5.8 to 20.0 wt. % $Al_2O_3$ and 0 to 6.0 wt. % $La_2O_3$;
b) the quantity of $Me(I)_2O$ quoted is formed of 3.0 to 15.0 wt. % $K_2O$, 3.0 to 12.0 wt. % $Na_2O$ and 0 to 2.5 wt. % $Li_2O$;
c) the quantity of $Me(II)O$ quoted is formed of 0 to 10.0 wt. % $CaO$, 0 to 7.5 wt. % $BaO$, 0 to 9 wt. % $MgO$, 0 to 3.5 wt. % $ZnO$ and 0 to 8.5 wt. % $SrO$; and
d) the quantity of $Me(IV)O_2$ quoted is formed of 0 to 5.0 wt. % $TiO_2$ and 0 to 5.0 wt. % $ZrO_2$.

All weight percentage data are relative to the glass.

It is preferred that the glass contains 0 to 0.9 wt. % $B_2O_3$. Particularly preferred are glasses which contain the following components.

| Component | Wt. % |
| --- | --- |
| $SiO_2$ | 53.0–62.0 |
| $B_2O_3$ | 0–0.9 |
| $Al_2O_3$ | 10.0–17.0 |
| $K_2O$ | 6.0–15.0 |
| $Na_2O$ | 5.0–11.0 |
| $CaO$ | 2.0–7.0 |
| $BaO$ | 0–5.5 |
| $SrO$ | 0–8.5 |
| $TiO_2$ | 0.2–2.0 |
| $ZrO_2$ | 0–3.0 |
| $P_2O_5$ | 2.0–5.0 |
| $CeO_2$ | 0–1.0 |

The opalescent glass according to the invention is formed in a conventional manner and in particular by melting suitable starting materials at a temperature of 1400° to 1650° C., with the formation of a homogeneous glass melt. If the opalescence effect of the glass produced in this way is sufficient, subsequent heat treatment need not be carried out. Since, however, the intensity of the opalescence effect can in general be increased by means of the heat treatment mentioned hereinafter, treatment of this kind is preferably to be carried out. During the heat treatment, the prepared glass melt, is kept for a certain period of time in the temperature range from 950° to 1100° C., after or without prior cooling to room temperature. This treatment preferably lasts 15 minutes to 4 hours.

By means of scanning electron microscopic investigation, it was proven that the glass according to the invention has a microheterogeneous structure, displaying a continuous glass phase in which a discontinuous glass phase is dispersed. The discontinuous glass phase exists in the form of drops which have an average size of about 150 to 250 nm, relative to the number of drops. The investigations likewise showed that the size distribution of the drops is narrow.

Surprisingly, it is possible to expose the glass according to the invention to the conditions which prevail during dental processing without the opalescence effect becoming impaired. The dental processing of the glass according to the invention as dental material involves that a granulate with a particle size of preferably less than 90 μm is formed from the glass and this granulate is then sintered together at temperatures of up to 1100° C., preferably 880° to 1070° C. Two to four further thermal treatments at temperatures of up to 1100° C. can be appended to this sintering together. Surprisingly, the glass according to the invention survives all these conditions without loss of the opalescence effect. Rather, it was established that in some cases the conditions of the dental processing even led to an increase in the opalescence effect. The glass according to the invention is therefore clearly superior to the glasses known to date which, under the dental processing conditions described, become completely transparent or very quickly crystallize out to a white opaque material, the result in both cases being a loss in the opalescence.

The high opalescence of the glasses according to the invention is all the more surprising since they contain relatively large quantities of $Al_2O_3$, namely 5.8 to 20.0 wt. %. With the silicate glasses known from DE-PS 2 313 074, such quantities of $Al_2O_3$ lead to a reduction or a complete disappearance of the opalescence effect.

In addition to a stable opalescence effect, the glasses according to the invention are also characterized by an excellent chemical resistance and by a linear expansion coefficient suitable for dental applications. The glasses according to the invention can therefore be used in an advantageous manner for dental applications. For this, the glasses can themselves be used as dental material or as a component of or additive to dental materials. The glasses according to the invention are particularly preferably used together with silicate glasses and silicate glass ceramics. Alone or combined with other compatible additives, the glasses according to the invention can be granulated as described and then sintered to give dense dental products, such as inlays, onlays, crowns or coating ceramics on metal. It is also possible to use the opalescent glass according to the invention as a filler for inlays, onlays or those moulded articles from which computer-milled dental replacement parts are produced.

The invention is further explained with reference to the following examples.

EXAMPLES

Examples 1 to 24

27 opalescent glasses according to the invention, which had the compositions shown in the following Table I, were prepared by melting at temperatures from 1400° to 1650° C., cooling to temperatures from 1100° C. to room temperature and optionally by subsequent heat treatment for 15 minutes to 4 hours in the temperature range from 950° to 1100° C.

Glasses 5, 8, 9, 14, 15, 20 and 22 and glasses 25, 26 and 27 are preferred.

TABLE I

Composition of the glasses

| Component | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| $SiO_2$ | 57,7 | 57,7 | 53,1 | 59,4 | 56,0 | 48,9 | 55,0 | 56,0 | 55,6 | 55,5 | 49,0 | 60,6 | 62,0 | 55,1 |
| $B_2O_3$ | — | 1,0 | — | 1,0 | 0,2 | 1,0 | — | — | 0,9 | 1,0 | — | — | — | 0,4 |
| $Al_2O_3$ | 13,5 | 13,7 | 12,8 | 14,3 | 15,8 | 13,9 | 12,8 | 10,4 | 13,1 | 5,9 | 19,3 | 12,8 | 14,0 | 12,8 |
| $La_2O_3$ | — | — | — | — | — | — | — | — | — | — | — | — | — | — |
| $K_2O$ | 7,3 | 7,3 | 7,0 | 7,8 | 11,0 | 7,3 | 7,0 | 10,0 | 7,0 | 8,0 | 3,1 | 3,0 | 7,9 | 6,9 |
| $Na_2O$ | 5,9 | 5,9 | 5,6 | 5,9 | 9,6 | 5,9 | 11,0 | 7,7 | 5,8 | 6,7 | 3,6 | 3,0 | 4,8 | 10,6 |
| $Li_2O$ | — | — | — | — | — | — | — | — | — | — | — | — | — | — |
| CaO | 5,9 | 5,9 | 5,8 | — | 2,6 | 5,9 | 5,6 | 5,3 | 5,8 | 10,0 | 7,6 | 7,7 | 6,4 | 5,6 |
| BaO | 4,7 | 4,7 | 4,5 | 4,8 | — | 4,7 | — | 4,2 | 4,9 | 5,9 | 7,5 | 4,4 | — | — |
| MgO | — | — | — | — | — | — | — | — | — | — | — | — | — | — |
| SrO | — | — | — | — | — | — | — | — | — | — | — | — | — | — |
| ZnO | — | — | 3,5 | — | — | — | — | — | — | — | — | — | — | — |
| $TiO_2$ | — | 1,3 | 1,8 | 1,4 | 0,3 | 5,0 | 1,2 | 1,8 | 1,4 | 1,5 | 2,4 | 1,7 | 1,4 | 1,1 |
| $ZrO_2$ | 2,6 | — | 3,0 | 2,7 | 1,9 | 5,0 | 2,4 | 2,4 | 2,8 | 2,9 | 5,0 | 3,3 | 2,8 | 2,5 |
| $P_2O_5$ | 2,4 | 2,5 | 2,9 | 2,7 | 2,6 | 2,4 | 5,0 | 2,2 | 2,7 | 2,7 | 2,5 | 3,5 | 0,6 | 5,0 |
| $CeO_2$ | — | — | — | — | — | — | — | — | — | — | — | — | — | — |

| Component | 15 | 16 | 17 | 18 | 19 | 20 | 21 | 22 | 23 | 24 | 25 | 26 | 27 |
|---|---|---|---|---|---|---|---|---|---|---|---|---|---|
| $SiO_2$ | 55,3 | 56,1 | 54,9 | 56,1 | 57,8 | 61,6 | 54,8 | 53,6 | 59,3 | 65,3 | 53,4 | 53,9 | 55,9 |
| $B_2O_3$ | 0,2 | — | 1,0 | — | — | — | — | 0,9 | 1,0 | — | 0,2 | 0,2 | 0,2 |
| $Al_2O_3$ | 16,1 | 13,3 | 13,2 | 12,5 | 13,6 | 14,5 | 12,9 | 12,6 | 13,9 | 5,8 | 16,5 | 16,6 | 16,6 |
| $La_2O_3$ | — | — | — | 6,0 | — | — | — | — | — | — | — | — | — |
| $K_2O$ | 11,9 | 7,1 | 7,9 | 7,2 | 7,4 | 7,9 | 7,0 | 6,9 | 7,6 | 3,3 | 14,5 | 14,3 | 10,3 |
| $Na_2O$ | 9,1 | 5,8 | 5,7 | 5,8 | 5,8 | 6,4 | 5,7 | 5,6 | 7,3 | 4,4 | 7,1 | 7,5 | 7,6 |
| $Li_2O$ | — | — | — | — | 2,5 | — | — | — | — | — | — | — | — |
| CaO | 2,6 | 5,8 | 5,7 | 5,9 | 6,1 | 6,5 | 5,8 | 5,7 | 3,5 | — | 2,6 | 2,6 | 5,6 |
| BaO | — | 4,9 | 4,8 | — | — | — | 4,6 | — | — | 4,8 | — | — | — |
| MgO | — | — | — | — | — | — | — | — | — | 8,2 | — | — | — |
| SrO | — | — | — | — | — | — | — | 8,5 | — | — | — | — | — |
| ZnO | — | — | — | — | — | — | — | — | — | — | — | — | — |
| $TiO_2$ | 0,3 | 1,4 | 1,4 | 1,3 | 1,4 | 0,5 | 1,3 | 1,3 | 1,4 | 1,9 | 0,3 | 0,3 | 0,3 |
| $ZrO_2$ | 1,9 | 2,8 | 2,7 | 2,6 | 2,7 | — | 2,6 | 2,5 | 2,8 | 3,6 | 1,9 | 1,9 | 0,9 |
| $P_2O_5$ | 2,6 | 2,8 | 2,7 | 2,5 | 2,6 | 2,7 | 2,4 | 2,4 | 3,3 | 2,7 | 2,6 | 2,6 | 2,6 |
| $CeO_2$ | — | — | — | — | — | — | 3,0 | — | — | — | 0,9 | — | — |

The properties of different selected glasses according to the invention are detailed in the following Table II.

TABLE II

Properties of selected glasses

| Glass no. | Heat treatment of the starting glass after pouring of the melt [°C./h] | Sintering temperature range for the production of rods for α-measurement [°C.] | Linear expansion coefficient α (100-500° C.) [°C.$^{-1}$] | $T_g$ [°C.] | $T_E$ [°C.] |
|---|---|---|---|---|---|
| 4 | none | 1000/1020 | $8.1 \times 10^{-6}$ | 677 | 778 |
| 5 | 950/0.5 h | 960/980 | $15.1 \times 10^{-6}$ | 553 | 670 |
| 6 | none | 960/980 | $9.1 \times 10^{-6}$ | 677 | 750 |
| 8 | none | 900/920 | $10.3 \times 10^{-6}$ | 598 | 664 |
| 9 | 950/1 h | 1020/1020 | $8.5 \times 10^{-6}$ | 654 | 740 |
| 9 | 1060/1 h | 1020/1020 | $8.4 \times 10^{-6}$ | 657 | 745 |
| 13 | 1050/2 h | 960/980 | $8.6 \times 10^{-6}$ | 672 | 748 |
| 14 | none | 960/980 | $10.8 \times 10^{-6}$ | 634 | 710 |
| 15 | 1000/1 h and 900/1 h | 960/980 | $16.8 \times 10^{-6}$ | 552 | 697 |
| 16 | 1000/1 h | 1020/1020 | $8.7 \times 10^{-6}$ | 682 | 766 |
| 18 | none | 1030/1050 | $8.6 \times 10^{-6}$ | 699 | 788 |
| 19 | none | 840/860 | $9.5 \times 10^{-6}$ | 561 | 629 |
| 20 | none | 1000/1020 | $8.6 \times 10^{-6}$ | 657 | 745 |
| 26 | 1040/1 h | 980/1000 | $18.2 \times 10^{-6}$ | 580 | 770 |
| 27 | 950/0.5 h | 960/980 | $17.6 \times 10^{-6}$ | 628 | 800 |

$T_g$ = Transformation temperature
$T_E$ = Softening temperature

Test-rods were prepared for the determination of the linear thermal expansion coefficient α. To this end, the selected glasses according to the invention were granulated to particle sizes of <90 μm and the obtained glass granulate sintered within the temperature ranges given in Table II to give rods. As Table II shows, the expansion coefficient can be controlled, depending on the glass composition, between $8.1 \times 10^{-6}$ and $18.2 \times 10^{-6}$ °C.$^{-1}$, measured in the temperature range of 100° to 500° C. Depending on the dental application, for example if the glass is to be used as additive for a baked-on ceramic or as additive for a pressed glass ceramic, it is therefore possible to produce a glass with a compatible expansion coefficient.

In this connection, glasses 5, 15, 25, 26 and 27 are to be emphasized in particular. Despite a very high expansion coefficient, they characterize themselves through an adequate to very good opalescence. With traditional glasses, high expansion coefficients can frequently only be attained with very marked losses of the opalescence effect. The glasses according to the invention, however, combine both properties in an advantageous way.

Table II also shows that the transformation ranges of the glasses lie between approximately 550° and 700° C. and the softening temperatures between approximately 620° and 800° C.

Quoted in the following Table III are qualitative values for the opalescence effect of the glasses according to the invention and values for their chemical resistance.

TABLE III

Properties of selected glasses

| Glass no. | Heat treatment of the starting glass after pouring of the melt [°C./h] | Sintering temperature range for the production of small test plates [°C.] (holding time 1 min) | Mass loss after treatment with acetic acid (according to ISO 6872-1984) [%] | Opalescence |
|---|---|---|---|---|
| 4 | none | 1020/1040 | 0.0059 | good |
| 5 | 960/1 h | 980/1020 | 0.0198 | adequate |
| 6 | none | 980/1000 | 0.0143 | adequate |
| 8 | none | 920/940 | 0.0058 | adequate |
| 9 | 950/1 h | 1000/1000 | 0.0052 | adequate |
| 9 | 1060/1 h | 1000/1020 | 0.0084 | very good |
| 13 | 1050/2 h | 1000/1020 | 0.0153 | adequate |
| 14 | none | 1000/1020 | 0.0092 | very good |
| 15 | 950/1 h | 980/970 | 0.0057 | very good |
| 16 | 1000/1 h | 1020/1000 | 0.0081 | good |
| 18 | none | 1050/1070 | 0.0060 | adequate |
| 19 | none | 880/900 | 0.0090 | good |
| 20 | none | 1020/1040 | 0.0063 | very good |
| 26 | 1040/1 h | 1010/1030 | 0.0348 | adequate |
| 27 | 950/0.5 h | 980/1000 | 0.0218 | good |

For the determination of the chemical resistance of the glasses according to the invention and their opalescence, small test plates were produced from the opalescent glass by sintering together granulate with a particle size of less than 90 μm within the temperature ranges given in Table III to give small plates with a diameter of 12 mm and a thickness of 1 mm. The granulate was held at the sintering temperature for 1 min.

To estimate the chemical resistance, the mass loss of the small test plates was determined after treatment with 4% acetic acid in a Soxhlet apparatus according to ISO 6872-1984. As the values given in Table III show, all glasses satisfied the standard of less than 0.05% mass loss. In view of a very low mass loss, the glasses preferred are nos. 4, 8, 15, 18 and 20.

The opalescence effects of the individual glasses were compared with one another and appraised qualitatively. The results of the appraisal are to be found in Table III. Because of their high opalescence, the glasses preferred are nos. 5, 9 (with heat treatment), 14, 15 and 20.

In order to also be able to determine quantitatively the opalescence of the glasses according to the invention, the so-called contrast value (CR-value) was determined for three different glasses according to British Standard Institution BSI 5612, 1978, paragraph 8.11. To this end, a light-optical measurement, compared with a white and black standard sample was carried out with a Minolta CR-300 apparatus on glass test plates having a diameter of 12 mm and a thickness of 1±0.025 mm.

The small glass test plates were again produced by sintering the glass granulate, and the measured contrast value and the qualitatively estimated opalescence are given in the following Table IV.

TABLE IV

| Glass no. | Heat treatment of the starting glass [°C./h] | Sintering conditions for the production of small test plates [°C/min.] | CR-value | Opalescence qualitatively |
|---|---|---|---|---|
| 15 | 1000/0.25 | 1020/1 | 0.8559 | very good |
| 16 | 1000/1 | 1020/1 | 0.7267 | good |
| 17 | 1000/1 | 1020/1 | 0.8524 | very good |

We claim:

1. Opalescent glass having a continuous glass phase and a discontinuous glass phase dispersed therein, and consisting essentially of the following components:

| Component | Wt. % |
|---|---|
| $SiO_2$ | 48.0 to 66.0 |
| $B_2O_3$ | 0 to 1.0 |
| $Me(III)_2O_3$ | 5.8 to 20.0 |
| $Me(I)_2O$ | 6.0 to 22.0 |
| $Me(II)O$ | 3.5 to 16.0 |
| $Me(IV)O_2$ | 0.5 to 10.0 |
| $P_2O_5$ | 0.5 to 5.0 |
| $CeO_2$ | 0 to 3.0 | where
a) the quantity of Me(III)$_2$O$_3$ quoted is formed of 5.8 to 20.0 wt. % $Al_2O_3$ and 0 to 6.0 wt. % $La_2O_3$;
b) the quantity of Me(I)$_2$O quoted is formed of 3.0 to 15.0 wt. % $K_2O$, 3.0 to 12.0 wt. % $Na_2O$ and 0 to 2.5 wt. % $Li_2O$;
c) the quantity of Me(II)O quoted is formed of 0 to 10.0 wt. % CaO, 0 to 7.5 wt. % BaO, 0 to 9.0 wt. % MgO, 0 to 3.5 wt. % ZnO and 0 to 8.5 wt. % SrO; and
d) the quantity of Me(IV)O$_2$ quoted is formed of 0 to 5.0 wt. % $TiO_2$ and 0 to 5.0 wt. % $ZrO_2$.

2. Opalescent glass according to claim 1, consisting essentially of 0 to 0.9 wt. % $B_2O_3$.

3. Opalescent glass according to claim 1, consisting essentially of the following components:

| Component | Wt. % |
|---|---|
| $SiO_2$ | 53.0–62.0 |
| $B_2O_3$ | 0–0.9 |
| $Al_2O_3$ | 10.0–17.0 |
| $K_2O$ | 6.0–15.0 |
| $Na_2O$ | 5.0–11.0 |
| CaO | 2.0–7.0 |
| BaO | 0–5.5 |
| SrO | 0–8.5 |
| $TiO_2$ | 0.2–2.0 |
| $ZrO_2$ | 0–3.0 |
| $P_2O_5$ | 2.0–5.0 |
| $CeO_2$ | 0–1.0. |

4. A process for producing an opalescent glass having a continuous phase and a discontinuous glass phase dispersed therein, the process comprising:
(1) melting starting materials to form a homogeneous glass melt comprising the following components:

| Component | Wt. % |
|---|---|
| $SiO_2$ | 48.0 to 66.0 |
| $B_2O_3$ | 0 to 1.0 |
| $Me(III)_2O_3$ | 5.8 to 20.0 |
| $Me(I)_2O$ | 6.0 to 22.0 |
| $Me(II)O$ | 3.5 to 16.0 |
| $Me(IV)O_2$ | 0.5 to 10.0 |
| $P_2O_5$ | 0.5 to 5.0 |
| $CeO_2$ | 0 to 3.0 | where
a) the quantity of Me(III)$_2$O$_3$ quoted is formed of 5.8 to 20.0 wt. % $Al_2O_3$ and 0 to 6.0 wt. % $La_2O_3$;
b) the quantity of Me(I)$_2$O quoted is formed of 3.0 to 15.0 wt. % $K_2O$, 3.0 to 12.0 wt. % $Na_2O$ and 0 to 2.5 wt. % $Li_2O$;
c) the quantity of Me(II)O quoted is formed of 0 to 10.0 wt. % CaO, 0 to 7.5 wt. % BaO, 0 to 9.0 wt. % MgO, 0 to 3.5 wt. % ZnO and 0 to 8.5 wt. % SrO; and
d) the quantity of Me(IV)O$_2$ quoted is formed of 0 to 5.0 wt. % $TiO_2$ and 0 to 5.0 wt. % $ZrO_2$; and thereafter optionally
(2) subjecting the glass prepared in step (1) to heat treatment in the range of from 950° C. to 1,100° C.

5. The process according to claim 4, wherein the heat treatment of step (2) is carried out for 15 minutes to 4 hours.

6. The process according to claim 4 including the additional step of granulating the opalescent glass into particles and sintering the granulate together at a temperature of up to 1100° C.

7. The process according to claim 6, wherein the sintering is effected by heating the granulate to 880° to 1070° C.

8. A dental material comprising the opalescent glass of claim 1.

9. An additive to silicate glasses or Silicate glass ceramics composed of the opalescent glass of claim 1.

10. A dental inlay, onlay, bridge or crown comprising the opalescent glass of claim 1.

* * * * *